United States Patent [19]
Bandman et al.

[11] Patent Number: 6,103,874
[45] Date of Patent: Aug. 15, 2000

[54] HUMAN KDEL RECEPTOR

[75] Inventors: Olga Bandman, Mountain View; Jennifer L. Hillman, San Jose; Surya K. Goli, Sunnyvale, all of Calif.

[73] Assignee: Incyte Pharmaceuticals, Inc., Palo Alto, Calif.

[21] Appl. No.: 09/133,735

[22] Filed: Aug. 13, 1998

Related U.S. Application Data

[62] Division of application No. 08/753,159, Nov. 21, 1996, Pat. No. 5,824,500.

[51] Int. Cl.$^7$ .......................... C07K 14/00; A61K 38/16; C07H 21/04
[52] U.S. Cl. .......................... 530/350; 435/7.1; 435/69.1; 514/2
[58] Field of Search .................................... 530/350, 300; 435/69.1; 514/2; 43/7.1

[56] References Cited

PUBLICATIONS

Gething, M.J. et al., "Protein folding in the cell.", *Nature* (1992) 355 (6355):33–45.
Munro, S. et al., "An Hsp 70–like protein in the ER: identity with the 78 kd glucose–regulated protein and immunoglobulin heavy chain binding protein.", *Cell* (1986) 46 (2):291–300.
Pelham, H.R., "Control of protein exit from the endoplasmic reticulum.", *Annu.Rev.Cell Biol.* (1989) 5:1–23.
Hardwick, K.G. et al., "ERD1, a yeast gene required for the retention of luminal endoplasmic reticulum proteins, affects glycoprotein processing in the Golgi apparatus.", *EMBO J.* (1990) 9 (3):623–630.
Semenza, J.C. et al., "ERD2, a Yeast Gene Required for the Receptor–Mediated Retrieval of Luminal ER Proteins from the Secretory Pathway.", *Cell* (1990) 61:1349–1357.
Lewis, M.J. et al., "A human homologue of the yeast HDEL receptor.", *Nature* (1990) 348:162–163.
Lewis, M.J. et al., "Sequence of a Second Human KDEL Receptor.", *J.Mol.Biol.* (1992) 226:913–916.
Lewis, M.J. et al., "Ligand–Induced Redistribution of a Human KDEL Receptor from the Golgi Complex to the Endoplasmic Reticulum", *Cell* (1992) 68:353–364.
Townsley, F.M. et al., "Retrieval of HDEL proteins is required for growth of yeast cells.", *J.Cell Biol.* (1994) 127 (1):21–28.
Hsu, V.W. et al., "A brefeldin A–like phenotype is induced by the overexpression of a human ERD–2–like protein, ELP–1.", *Cell* (1992) 69 (4):625–635.
Pathak, R.K. et al., "Immunocytochemical localization of mutant low density lipoprotein receptors that fail to reach the Golgi complex.", *J.Cell Biol.* (1988) 106 (6):1831–1841.
Kim, P.S. et al., "An endoplasmic reticulum storage disease causing congenital goiter with hypothyroidism.", *J.Cell Biol.* (1996) 133 (3):517–527.
Gow, A. et al., "Many naturally occurring mutations of myelin proteolipid protein impair its intracellular transport.", *J.Neurosci.Res.* (1994) 37 (5):574–583.

Kakiuchi, T. et al., "Inhibition by brefeldin A of the specific B cell antigen presentation to MHC class II–restricted T cells.", *J.Immunol.* (1991) 147 (10):3289–3295.
Wilson, D.W. et al., "pH–dependent binding of KDEL to Its Receptor in Vitro", *J.Biol.Chem.* (1993) 268 (10):7465–7468.
Adams, M.D. et al., "Initial assessment of human gene diversity and expression patterns based upon 83 million nucleotides of cDNA sequence", *Nature* 377: 3–17 (1995).
EMBL Sequence Database, Heidelberg, De, Accession NR.: AA296832, Apr. 18, 1997, M.D. Adams et al. "cDNA 5' End Similar to Kdel Receptor".
EMBL Sequence Databse, Heidelberg, De, Accession NR.: AA298677, Apr. 18, 1997, M.D. Adams et al. "cDNA 5' End Similar to Kdel Receptor".
EMBL Sequence Databse, Heidelberg, De, Accession NR.: N94475, Apr. 19, 1996, L. Hillier et al. "cDNA Clone Similar to ER Lumen Protein Retaining Receptor 2 (Human)" XP002059460.
EMBL Sequence Databse, Heidelberg, De, Accession NR.: W21175, May 8, 1996, L. Hillier et al. "Human cDNA Clone Similar to ER Lumen Protein Retaining Receptor 2" XP002059461.
EMBL Sequence Databse, Heidelberg, De, Accession NR.: W23902, May 9, 1996, L. Hillier et al. "Human cDNA Similar to ER Lumen Protein Receptor 1" XP002059462.
Scheel, A.A. and R.B. Pelham, "Purification and Characterization of the Human KDEL Receptor", *Biochemistry*, 35: 10203–10209 (1996).
Lewis, M.J. and H.R.B. Pelham, "A Human Homologue of the yeast HDEL receptor", *Nature*, 348: 162–163 (1990).
EMBL Sequence Database, Heidelberg, De, Accession NR.: Z97056, Jun. 20, 1997, R Connor, "Human cDNA Similar to Lumen Protein Retaining Receptor 2 (Kdel Receptor 2)" XP002059463.
Wallace et al., *Methods in Enzymology*, 152:432–442 (1987).

*Primary Examiner*—Elizabeth Kemmerer
*Assistant Examiner*—Nirmal S. Basi
*Attorney, Agent, or Firm*—Incyte Pharmaceuticals, Inc.

[57] ABSTRACT

The present invention provides a novel human KDEL receptor (NHKR) and polynucleotides which identify and encode NHKR. The invention also provides genetically engineered expression vectors and host cells comprising the nucleic acid sequences encoding NHKR and a method for producing NHKR. The invention also provides for agonists, antibodies, or antagonists specifically binding NHKR, and their use, in the prevention and treatment of diseases associated with expression of NHKR. Additionally, the invention provides for the use of antisense molecules to polynucleotides encoding NHKR for the treatment of diseases associated with the expression of NHKR. The invention also provides diagnostic assays which utilize the polynucleotide, or fragments or the complement thereof, and antibodies specifically binding NHKR.

5 Claims, 8 Drawing Sheets

```
5' TGG CAG CCG CCC TGC CCA GAA AGT TTC CCC CTA AGT TTG CTG GGC GCG GGC          54

GCA CGA ACT GGC TGG ACC ATG AAC GTG TTC CGA ATC CTC GGC GAC CTG ATC         108
     A   R   T   G   W   T   M   N   V   F   R   I   L   G   D   L   I

CAC CTC GCC ATG ATC TTG CTG CTG GGG AAT ATC TGG AGG TCC AAG TGC TGC         162
     H   L   A   M   I   L   L   L   G   N   I   W   R   S   K   C   C

AAG GGC ATC TCT GGG AAA AGC CAG ATC CTG TTT GCT CTC GTC TTC ACC ACC AGG     216
     K   G   I   S   G   K   S   Q   I   L   F   A   L   V   F   T   T   R

TAC CTG GAC CTG TTC ACC AAC TTC ATC TCC ATC TAC AAC ACA GTA ATG AAG GTG     270
     Y   L   D   L   F   T   N   F   I   S   I   Y   N   T   V   M   K   V

GTT TTT CTC CTC TGT GCC TAT GTT ACA GTG TAC ATG ATA TAT GGG AAA TTC CGT     324
     V   F   L   L   C   A   Y   V   T   V   Y   M   I   Y   G   K   F   R

AAA ACT TTT GAC AGT GAG AAT GAC ACA TTC CGC CTG GAG TTT CTT CTG GTC CCA     378
     K   T   F   D   S   E   N   D   T   F   R   L   E   F   L   L   V   P
```

FIGURE 1A

```
      387       396       405       414       423       432
GTC ATT GGC CTT TCC TTC CTT GAA AAC TAC AGT TTC ACT CTG GAG ATC CTC
 V   I   G   L   S   F   L   E   N   Y   S   F   T   L   E   I   L 441       450       459       468       477       486
TGG ACT TTC TCT ATC TAT CTG GAA TCA GTG GCT ATC CTG CCC CAG CTC TTC ATG
 W   T   F   S   I   Y   L   E   S   V   A   I   L   P   Q   L   F   M 495       504       513       522       531       540
ATC AGC AAG ACT GGA GAG GCT GAG ACC ATA ACT ACT CAC TAC CTG TNC TTT CTG
 I   S   K   T   G   E   A   E   T   I   T   T   H   Y   L   X   F   L 549       558       567       576       585       594
GGT CTG TAC CGG GCA CTC TAC CTG GCT AAC TGG ATC AGG CGG TAC CAG ACT GAG
 G   L   Y   R   A   L   Y   L   A   N   W   I   R   R   Y   Q   T   E 603       612       621       630       639       648
AAT TTC TAT GAC CAA ATT GCA GTC GTG TCT GGA GTA CAA ACC ATC TTC TAC
 N   F   Y   D   Q   I   A   V   V   S   G   V   Q   T   I   F   Y 657       666       675       684       693       702
TGT GAC TTC TTC TAC TTG TAT GTG ACC AAA GTC CTT AAG GGA AAG AAG TTA AGT
 C   D   F   F   Y   L   Y   V   T   K   V   L   K   G   K   K   L   S 711       720       729       738       747       756
CTT CCA ATG CCA ATC TGA GGA CCT TCA GAG ACA GTC TAC GCC TTA ACA AGC ACA
 L   P   M   P   I
```

FIGURE 1B

```
            765            774            783     792            801            810
TGA AGG AAA CTN TTT TGA ATG TTC TCT TTG GCA ACT TAT CCA TAA TTT GGG ATC 819            828            837     846            855            864
AAA TGT TAA AAC CAG AAA AGT GTT TAG TGT GGA TTT CAG CAA AAC CTG ATC ATC 873            882            891     900            909            918
CCA CCC AGA AGA CCT TCT CAT CAA TAG ATC GCC CTT AAA GAC CCA TTG TAA GGT 927            936            945     954            963            972
CAT AAA AAA CCT CGG CCA ACT GCA CAA AGA TGG TGC CTC ACT GCA ACA AGA AAC 981            990            999     1008           1017           1026
CTT AAG GTG TCT TAC CGA CGN AAT AAA AAA CAT AAA TGA TTG TTC TCC TCT TAG 1035           1044           1053    1062           1071
AAT GTC CCA ACT AAA GAC CAG TTA AAA TAT TAG GGT ACG TTC TTG TG 3'
```

FIGURE 1C

```
  1   M D Q K S L W A G V V V L L L L Q G G S A Y K L V C Y F T N W S Q D R Q E P G K   SEQ ID NO:1
  1   M G V K A S Q T G F V V L V L L Q C C S A Y K L V C Y Y T S W S Q Y R E G D G S   GI 348912
  1   M V R S V A W A G F M V L L M I P W G S A A K L V C Y F T N W A Q Y R Q G E A R   GI 1050958

41   F T P E N I D P F L C S H L I Y S F A S I E N N K V I I K D K S E V M L Y Q T I   SEQ ID NO:1
 41   C F P D A L D R F L C T H I I Y S F A N I S N D H I D T W E N D V T L Y G M L   GI 348912
 41   F L P K D L D P S L C T H L I Y A F A G M T N H Q L S T T E W N D E T L Y Q E F   GI 1050958

81   N S L K T K N P K L K I L L S I G G Y L F G S K G F H P M V D S S T S R L E F I   SEQ ID NO:1
 81   N T L K N R N P N L K T L L S V G G W N F G S Q R F S K I A S N T Q S R R T F I   GI 348912
 81   N G L K K M N P K L K T L L A I G G W N F G T Q K F T D M V A T A N N R Q T F V   GI 1050958

121   N S I L F L R N H N F D G L D V S W I Y P D Q K - - - - - E N T H F T V L I H    SEQ ID NO:1
121   K S V P P F L R T H G F D G L D L A W L Y P G R R - - - - - D K Q H F T T L I K   GI 348912
121   N S A I R F L R K Y S F D G L D W E Y P G S Q G S P A V D K E R F T T L V Q       GI 1050958

156   E L A E A F Q K D F T K S T K E R L L L T A G V S A G R Q M I D N S Y Q V E K L   SEQ ID NO:1
156   E M K A E F I K E A Q - P G K K Q L L L S A A A L S A G K V T I D S S Y D I A K I GI 348912
161   D L A N A F Q Q E A Q T S G K E R L L L S A A V P A G Q T Y V D A G Y E V D K I   GI 1050958

196   A K D L D F I N L L S F D F H G S W E K P L I T G H N S P L S K G W Q D R G P S   SEQ ID NO:1
195   S Q H L D F I S I M T Y D F H G A W R G - - T T G H H S P L F R G Q E D A S P D   GI 348912
201   A Q N L D F V N L M A Y D F H G S W E K - - V T G H N S P L Y K R Q E E S G A A   GI 1050958
```

FIGURE 2A

```
236  S Y Y N V E Y A V G Y W I H K G M P S E K V V M G I P T Y G H S F T L A S A - E    SEQ ID NO:1
233  R F S N T D Y A V G Y M L R L G A P A S K L V M G I P T F G R S F T L A S S - E    GI 348912
239  A S L N V D A A V Q Q W L Q K G T P A S K L I L G M P T Y G R S F T L A S S D     GI 1050958

275  T T V G A P A S G P G A A G P I T E S S G F L A Y Y E I C Q F L K G A K I T R L    SEQ ID NO:1
272  T G V G A P I S G P G I P G R F T K E A G T L A Y Y E I C D F L R G A T V H R T    GI 348912
279  T R V G A P A T G S G T P G P F T K E G G M L A Y Y E V C S W - K G A T K Q R I    GI 1050958

315  Q D Q Q V P Y A V K G N Q W V G Y D D V K S M E T K V Q F L K N L N L G G A M I    SEQ ID NO:1
312  L G Q Q V P Y A T K G N Q W V G Y D D Q E S V K S K V Q Y L K D R Q L A G A M V    GI 348912
318  Q D Q K V P Y I F R D N Q W V G F D D V E S F K T K V S Y L Q K G L G G A M V     GI 1050958

355  W S I D M D D F T G K S C N Q G - P Y P L V Q A V K R S L - - - - - - - - - -    SEQ ID NO:1
352  W A L D D F Q G S F C G Q D L R F P L T N A I K D A L A A T - - - - - - - -    GI 348912
358  W A L D D F A G F S C N Q G - R Y P L I Q T L R Q E L S L P Y L P S G T P E    GI 1050958

383  - - - - - - - - - - - - - - - - - - - - - - - - - - - - - - -                     SEQ ID NO:1
383  - - - - - - - - - - - - - - - - - - - - - - - - - - - - - - -                     GI 348912
397  L E V P K P G Q P S E P E H G P S P G Q D T F C Q G K A D G L Y P N P R E R S S    GI 1050958

383  - - - - - G S L                                                                    SEQ ID NO:1
383  - - - - - - - -                                                                   GI 348912
437  F Y S C A A G R L F Q Q S C P T G L V F S N S C K K C C T W N                     GI 1050958
```

FIGURE 2B

HUMAN KDEL RECEPTOR

This application is a divisional application of U.S. application Ser. No. 08/753,159, filed Nov. 21, 1996 now U.S. Pat. No. 5,824,500.

FIELD OF THE INVENTION

This invention relates to nucleic acid and amino acid sequences of a novel human KDEL receptor and to the use of these sequences in the study, diagnosis, and treatment of diseases of the cellular secretory pathway.

BACKGROUND OF THE INVENTION

The normal functioning of the eukaryotic cell requires that all newly synthesized proteins be correctly folded, modified, and delivered to specific inter and extracellular sites. Newly synthesized membrane and secretory proteins enter a cellular sorting and distribution network during or immediately after synthesis (cotranslationally or posttranslationally) and are routed to specific locations inside and outside of the cell. The initial compartment in this process is the endoplasmic reticulum (ER) where proteins undergo modifications such as glycosylation, disulfide bond formation, and assembly into oligomers. The proteins are then transported through an additional series of membrane-bound compartments which include the various cisternae of the Golgi complex, where further carbohydrate modifications occur. Transport between compartments occurs by means of vesicles that bud and fuse in a specific manner; once within the secretory pathway, proteins do not have to cross a membrane to reach the cell surface.

The complexity of this system has advantages for the cell because it allows proteins to fold and mature in closed compartments that contain the appropriate enzyme catalysts. It is, however, dependent on sorting mechanisms that position the enzymes correctly and maintain them in place.

The first organelle in this system, the ER, contains multiple enzymes involved in protein structure modifications. Among these are BiP (binding protein) which directs the correct folding of proteins and, PDI (protein disulfide isomerase) and a homologue of the 90 kDa heat-shock protein, both of which catalyze the formation and rearrangement of disulfide bonds (Gething, M. J. and Sambrook, J. (1992) Nature 355:33–45). These abundant soluble proteins must be retained in the ER and must be distinguished from the newly synthesized secretory proteins which are rapidly transported to the Golgi apparatus. The signal for retention in the ER in mammalian cells consists of the tetrapeptide sequence, KDEL, located at the carboxy terminus of proteins. This sequence was first identified when the sequences of rat BiP and PDI were compared and it was subsequently found at the carboxy terminus of other luminal ER proteins from a number of species (Munro, S. (1986) Cell 46:291–300; Pelham, H. R. (1989) Ann. Rev. Cell. Biol. 5:1–23). Proteins containing this sequence leave the ER but are quickly retrieved from the early Golgi compartment and returned to the ER, while proteins without this signal continue through the distribution pathway.

Two endoplasmic retrieval receptors were first identified in S. cerevesiae; two human endoplasmic retrieval receptors were subsequently isolated by the use of degenerate PCR primers based on the S. cerevesiae sequences (Hardwick, K. G. (1990) EMBO J. 9:623–630; Semenza, J. C. (1990) Cell 61:1349–1357; Lewis, M. J. and Pelham, H. R. (1990) Nature 348:162–163; Lewis, M. J. and Pelham, H. R. (1992) J. Mol. Biol. 226:913–916). Comparisons of these sequences shows that they consist of a conserved 7-transmembrane domain structure with only short loops in the cell cytoplasm and the ER lumen. Studies with these endoplasmic retrieval receptors show that ligand binding controls the movement of the receptor; when expressed in COS cells, the human receptor is normally concentrated in the Golgi, but moves to the ER when bound to a ligand such as KDEL-tagged hen lysozyme (Lewis, M. J. and Pelham, H. R. (1992) Cell 68:353–364).

The ER retrieval function of these molecules serves to maintain the pool of enzymes in the ER that are necessary to perform protein structure modifications, retains newly synthesized proteins in the ER until they have been correctly modified, and regulates the structure of the Golgi apparatus. Saccharomyces cerevisiae cells that lack an ER retrieval receptor (Erd2) have a defective Golgi apparatus and fail to grow. Analysis of yeast Erd2 mutants suggests that their growth requires both the retention of multiple proteins in the ER and the selective removal of specific proteins from the Golgi (Townsley, F. M. (1994) J. Cell Biol. 127:21–28). Overexpression of a human ER retrieval receptor in COS cells results in hyperactive retrograde traffic from the Golgi to the ER leading to a loss of the Golgi structure and the breakdown of the secretory pathway (Hsu V. W. (1992) Cell 69:625–635).

Disruptions in the cellular secretory pathway have been implicated in several human diseases. In familial hypercholesterolemia the low density lipoprotein receptors remain in the ER, rather than moving to the cell surface (Pathak, R. K. (1988) J. Cell Biol. 106:1831–1841). A form of congenital hypothyroidism is produced by a deficiency of thyroglobulin, the thyroid prohormone. In this disease the thyroglobulin is incorrectly folded and is therefore retained in the ER (Kim, P. S. (1996) J.Cell Biol. 133:517–527). Mutant forms of proteolipid protein (PLP) have been examined as they play a role in generating dysmyelinating or hypomyelinating diseases. In this case, the mutations that result in disease are mutations that arrest transport of PLP in the ER and the early Golgi; the subsequent accumulation of PLP in the ER results in rapid oligodendrocyte death (Gow, A. (1994) J. Neurosci. Res. 37:574–583).

The human ER retrieval receptor function is necessary for processing and presentation of specific antigens to T cells. Many antigens must be processed intracellularly before they can be presented, in association with major histocompatability complex (MHC) molecules at the cell surface, for recognition by the antigen-specific receptor of T cells. Disruption of the ER retrieval receptor function with an antibiotic, Brefeldin A, abolishes the ability of a cell to present these specific antigen complexes to T cells. These antigenic proteins must be retained in the ER for cleavage to smaller peptides which can then bind to MHC molecules and be released for presentation at the cell surface. (Kakiuchi, T. (1991) J. Immunol. 147:3289–3295).

The discovery of polynucleotides encoding a novel human KDEL receptor, and the molecules themselves, provides the means to further investigate the regulation of the cellular protein secretory pathway. Discovery of molecules related to a novel human KDEL receptor satisfies a need in the art by providing a means or a tool for the study of this pathway and the diseases that involve the dysfunction of this pathway.

SUMMARY OF THE INVENTION

The present invention features a novel human KDEL receptor hereinafter designated NHKR and characterized as having chemical and structural homology to human KDEL receptor GI 31218 and human KDEL receptor GI 119543. Accordingly, the invention features a substantially purified NHKR having the amino acid sequence, SEQ ID NO:1.

One aspect of the invention features isolated and substantially purified polynucleotides that encode NHKR. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode NHKR. The present invention also features antibodies which bind specifically to NHKR, and pharmaceutical compositions comprising substantially purified NHKR. The invention also features the use of agonists and antagonists of NHKR.

BRIEF DESCRIPTION OF THE FIGURES

FIGS. 1A, 1B and 1C show the amino acid sequence (SEQ ID NO:1) and nucleic acid sequence (SEQ ID NO:2) of NHKR. The alignment was produced using MACDNASIS PRO software (Hitachi Software Engineering Co., Ltd., San Bruno, Calif.).

FIGS. 2A and 2B show the amino acid sequence alignments among NHKR (SEQ ID NO:1), GI 31218 (SEQ ID NO:3), and GI 119543 (SEQ ID NO:4). The alignment was produced using the multisequence alignment program of DNASTAR™ software (DNASTAR Inc, Madison Wis.).

DESCRIPTION OF THE INVENTION

Figure 3:
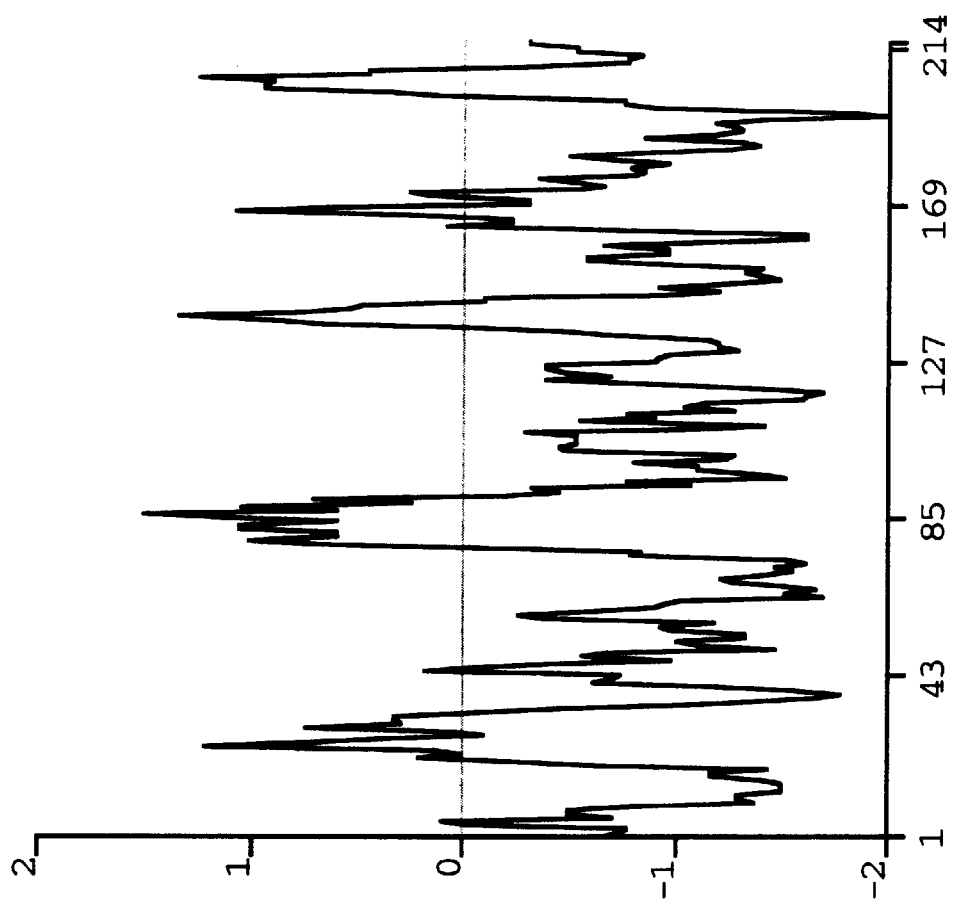
FIG. 3 shows the hydrophobicity plot (MacDNASIS PRO software) for NHKR, SEQ ID NO:1; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

NHKR, as used herein, refers to the amino acid sequences of substantially purified NHKR obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (Perkin Elmer, Norwalk, Conn.) in the 5' and/or the 3' direction and resequenced, or which has been assembled from the overlapping sequences of more than one Incyte clone using the GELVIEW Fragment Assembly system (GCG, Madison, Wis.), or which has been both extended and assembled.

A "variant" of NHKR, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic NHKR, or any oligopeptide thereof, to induce a specific immune response in appropriate animals or cells and to bind with specific antibodies.

The term "agonist", as used herein, refers to a molecule which, when bound to NHKR, causes a change in NHKR which modulates the activity of NHKR. Agonists may include proteins, nucleic acids, carbohydrates, or any other molecules which bind to NHKR.

The terms "antagonist" or "inhibitor", as used herein, refer to a molecule which, when bound to NHKR, blocks or modulates the biological or immunological activity of NHKR. Antagonists and inhibitors may include proteins, nucleic acids, carbohydrates, or any other molecules which bind to NHKR.

The term "modulate", as used herein, refers to a change or an alteration in the biological activity of NHKR. Modulation may be an increase or a decrease in protein activity, a change in binding characteristics, or any other change in the biological, functional or immunological properties of NHKR.

The term "mimetic", as used herein, refers to a molecule, the structure of which is developed from knowledge of the structure of NHKR or portions thereof and, as such, is able to effect some or all of the actions of novel human KDEL receptor-like molecules.

The term "derivative", as used herein, refers to the chemical modification of a nucleic acid encoding NHKR or the encoded NHKR. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm–5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human NHKR and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding NHKR or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding NHKR in a sample and thereby correlates with expression of the transcript from the polynucleotide encoding the protein.

"Alterations" in the polynucleotide of SEQ ID NO: 2, as used herein, comprise any alteration in the sequence of polynucleotides encoding NHKR including deletions, insertions, and point mutations that may be detected using hybridization assays. Included within this definition is the detection of alterations to the genomic DNA sequence which encodes NHKR (e.g., by alterations in the pattern of restriction fragment length polymorphisms capable of hybridizing to SEQ ID NO:2), the inability of a selected fragment of SEQ ID NO: 2 to hybridize to a sample of genomic DNA (e.g., using allele-specific oligonucleotide probes), and improper or unexpected hybridization, such as hybridization to a locus other than the normal chromosomal locus for the polynucleotide sequence encoding NHKR (e.g., using fluorescent in situ hybridization (FISH) to metaphase chromosomes spreads).

As used herein, the term "antibody" refers to intact molecules as well as fragments thereof, such as Fa, $F(ab)_2$, and Fv, which are capable of binding the epitopic determinant. Antibodies that bind NHKR polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human KDEL receptor, (NHKR), the polynucleotides encoding NHKR, and the use of these compositions for the diagnosis, prevention, or treatment of diseases of the cellular protein secretory pathway.

Nucleic acids encoding the human NHKR of the present invention were first identified in Incyte Clone 364214 from the PROSNOT01 cDNA library through a computer-generated search for amino acid sequence alignments. A consensus sequence, SEQ ID NO:2, was derived from the following overlapping and/or extended nucleic acid sequences: Incyte Clones (and cDNA libraries from which derived) 364214 (PROSNOT01); 350031 (LVENNOT01); 38492 (HUVENOB01); and 1856520 (PROSNOT18).

Figure 4:
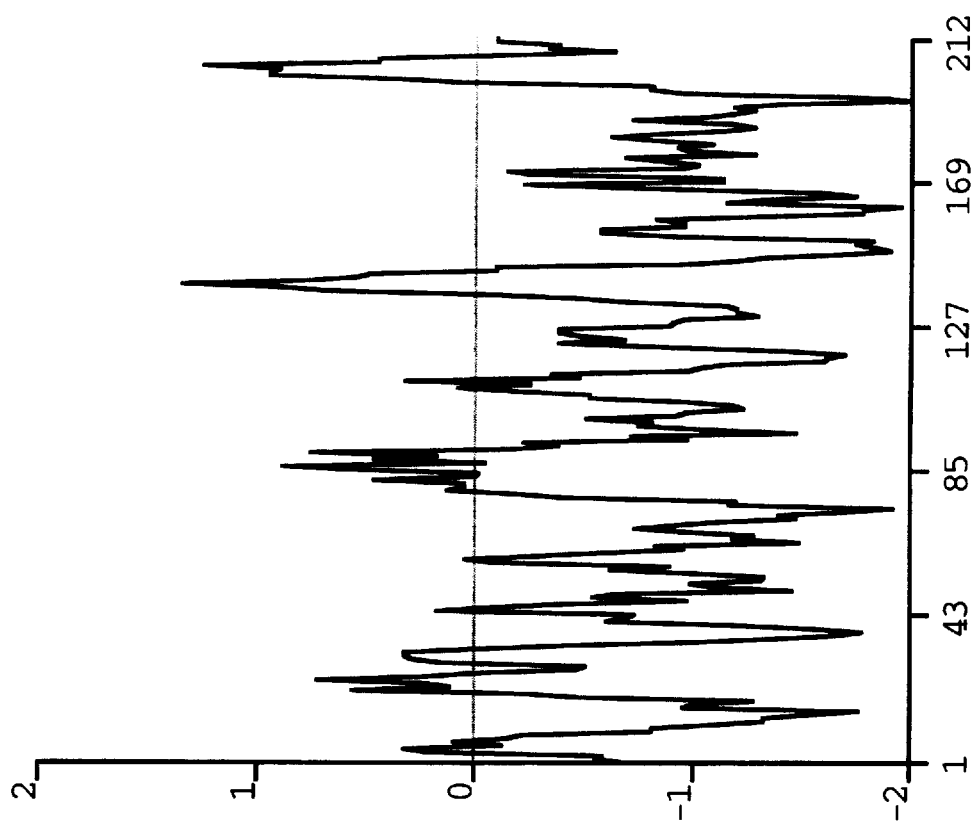
FIG. 4 shows the hydrophobicity plot for GI 31218, SEQ ID NO:3.
Figure 5:
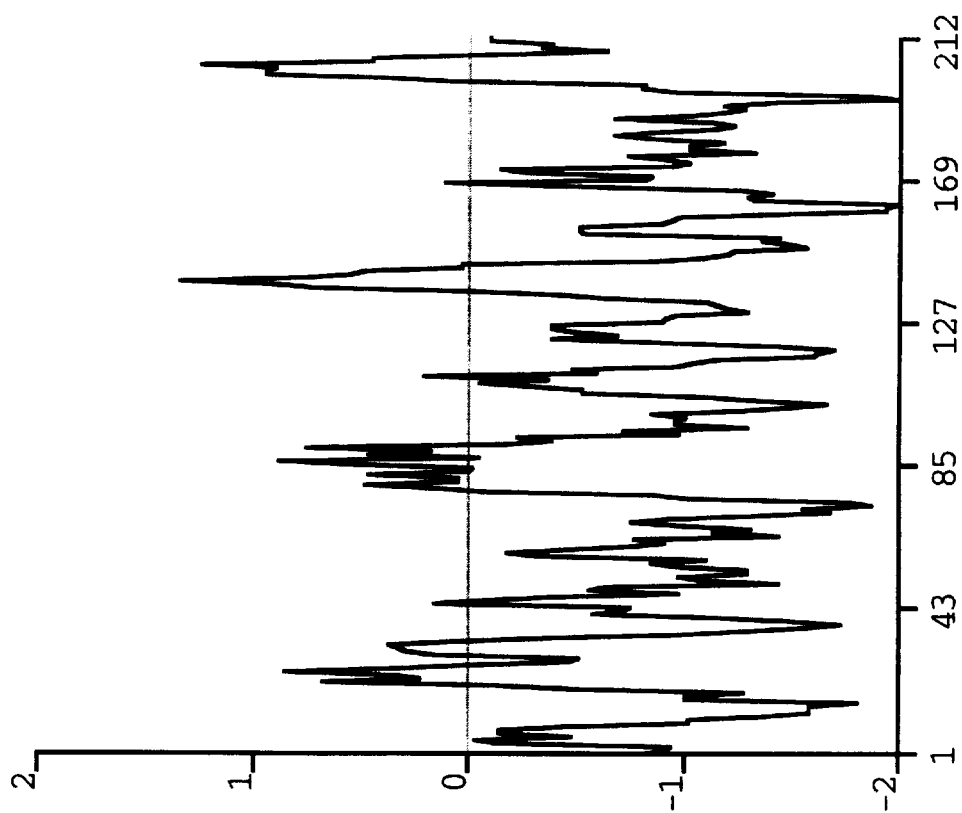
FIG. 5 shows the hydrophobicity plot for GI 119543, SEQ ID NO:4.

In one embodiment, the invention encompasses the novel human KDEL receptor, (NHKR), a polypeptide comprising the amino acid sequence of SEQ ID NO:1, as shown in FIGS. 1A, 1B and 1C. NHKR is 214 amino acids in length and has a potential glycosylation site, $N_{54}$ located in a putative ER luminal segment. NHKR has chemical and structural homology with GI 31218 (SEQ ID NO:3), and GI 119543 (SEQ ID NO:4). In particular, NHKR and GI 31218 and GI 119543 share 74% and 71% identity, respectively. As illustrated by FIGS. 3, 4, and 5, NHKR and GI 31218 and GI 119543 have similar hydrophobicity plots indicating similar functions.

The invention also encompasses NHKR variants. A preferred NHKR variant is one having at least 80%, and more preferably 90%, amino acid sequence similarity to the NHKR amino acid sequence (SEQ ID NO:1). A most preferred NHKR variant is one having at least 95% amino acid sequence similarity to SEQ ID NO:1.

The invention also encompasses polynucleotides which encode NHKR. Accordingly, any nucleic acid sequence which encodes the amino acid sequence of NHKR can be used to generate recombinant molecules which express NHKR. In a particular embodiment, the invention encompasses the polynucleotide comprising the nucleic acid sequence of SEQ ID NO:2 as shown in FIGS. 1A, 1B and 1C.

It will be appreciated by those skilled in the art that as a result of the degeneracy of the genetic code, a multitude of nucleotide sequences encoding NHKR, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring NHKR, and all such variations are to be considered as being specifically disclosed.

Although nucleotide sequences which encode NHKR and its variants are preferably capable of hybridizing to the nucleotide sequence of the naturally occurring NHKR under appropriately selected conditions of stringency, it may be advantageous to produce nucleotide sequences encoding NHKR or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding NHKR and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode NHKR and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding NHKR or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding NHKR which are encompassed by the invention include deletions, insertions, or substitutions of different nucleotides resulting in a polynucleotide that encodes the same or a functionally equivalent NHKR. The encoded protein may also contain deletions, insertions, or substitutions of amino acid residues which produce a silent change and result in a functionally equivalent NHKR. Deliberate amino acid substitutions may be made on the basis of similarity in polarity, charge, solubility, hydrophobicity, hydrophilicity, and/or the amphipathic nature of the residues as long as the biological activity of NHKR is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding NHKR. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding NHKR may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode NHKR, or fusion proteins or functional equivalents thereof, may be used in recombinant DNA molecules to direct expression of NHKR in appropriate host cells. Due to the inherent degeneracy of the genetic code, other DNA sequences which encode substantially the same or a functionally equivalent amino acid sequence may be produced and these sequences may be used to clone and express NHKR.

As will be understood by those of skill in the art, it may be advantageous to produce NHKR-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter NHKR encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding NHKR may be ligated to a heterologous sequence to encode a fusion protein. For example, to screen peptide libraries for inhibitors of NHKR activity, it may be useful to encode a chimeric NHKR protein that can be recognized by a commercially available antibody. A fusion protein may also be engineered to contain a cleavage site located between the NHKR encoding sequence and the heterologous protein sequence, so that NHKR may be cleaved and purified away from the heterologous moiety.

In another embodiment, sequences encoding NHKR may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of NHKR, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of NHKR, or any part thereof, may be altered during direct synthesis and/or combined using chemical methods with sequences from other proteins, or any part thereof, to produce a variant polypeptide.

In order to express a biologically active NHKR, the nucleotide sequences encoding NHKR or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding NHKR and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding NHKR. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding NHKR, vectors based on SV40 or EBV may be used with an appropriate selectable marker.

In bacterial systems, a number of expression vectors may be selected depending upon the use intended for NHKR. For example, when large quantities of NHKR are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding NHKR may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding NHKR may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express NHKR. For example, in one such system, *Autographa californica* nuclear polyhedrosis virus (AcNPV) is used as a vector to express foreign genes in *Spodoptera frugiperda* cells or in Trichoplusia larvae. The sequences encoding NHKR may be cloned into a non-essential region of the virus, such as the polyhedrin gene, and placed under control of the polyhedrin promoter. Successful insertion of NHKR will render the polyhedrin gene inactive and produce recombinant virus lacking coat protein. The recombinant viruses may then be used to infect, for example, *S. frugiperda* cells or Trichoplusia larvae in which NHKR may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding NHKR may be ligated into an adenovirus transcription/translation complex consisting of the late promoter and tripartite leader sequence. Insertion in a non-essential E1 or E3 region of the viral genome may be used to obtain a viable virus which is capable of expressing NHKR in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding NHKR. Such signals include the ATG initiation codon and adjacent sequences. In cases where sequences encoding NHKR, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express NHKR may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding NHKR is inserted within a marker gene sequence, recombinant cells containing sequences encoding NHKR can be identified by the absence of marker gene function. Alternatively, a marker gene can be placed in tandem with a sequence encoding NHKR under the control of a single promoter. Expression of the marker gene in response to induction or selection usually indicates expression of the tandem gene as well.

Alternatively, host cells which contain the nucleic acid sequence encoding NHKR and express NHKR may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding NHKR can be detected by DNA-DNA or DNA-RNA hybridization or amplification using probes or portions or fragments of polynucleotides encoding NHKR. Nucleic acid amplification based assays involve the use of oligonucleotides or oligomers based on the sequences encoding NHKR to detect transformants containing DNA or RNA encoding NHKR. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of NHKR, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on NHKR is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding NHKR include oligolabeling, nick translation, end-labeling or PCR amplification using a labeled nucleotide. Alternatively, the sequences encoding NHKR, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding NHKR may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode NHKR may be designed to contain signal sequences which direct secretion of NHKR through a prokaryotic or eukaryotic cell membrane. Other recombinant constructions may be used to join sequences encoding NHKR to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and NHKR may be used to facilitate purification. One such expression vector provides for expression of a fusion protein containing NHKR and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying NHKR from the fusion protein. A discussion of vectors which contain fusion proteins is provided in Kroll, D. J. et al. (1993; DNA Cell Biol. 12:441–453).

In addition to recombinant production, fragments of NHKR may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of NHKR may be chemically synthesized separately and combined using chemical methods to produce the full length molecule.

THERAPEUTICS

Based on the chemical and structural homology among NHKR (SEQ ID NO:1) and other human KDEL receptors, NHKR appears to function as an endoplasmic reticulum retrieval receptor.

In one embodiment vectors expressing NHKR may be administered to increase the level of NHKR in conditions characterized by defective functioning of the Golgi apparatus, low levels of NHKR expression, and diminished antigen processing capacity.

In one embodiment, vectors expressing antisense of the polynucleotides encoding NKHR may be administered to a subject to suppress the expression of NKHR, for treatment of ER storage diseases including, but not limited to, hypercholesterolemia and hypothyroidism.

In another embodiment, antagonists or inhibitors of NHKR may be administered to suppress the expression of NKHR for treatment of ER storage diseases including, but not limited to, hypercholesterolemia and hypothyroidism It also appears that NHKR is necessary for the growth of eukaryotic organisms, as demonstrated with *Saccharomyces cerevisiae* mutants. Therefore, in another embodiment antagonists of NHKR may be administered to a subject for the treatment of infections including but not limited to, those caused by fungal and protzoan organisms such as *Saccharomyces cerevisiae* and *Giardia lamblia*.

In another embodiment of the invention, supplying NHKR, a derivative thereof, or a vector expressing it, to mammalian cell lines may be useful in the study of the mechanisms of endoplasmic reticulum and early Golgi storage diseases.

Antagonists or inhibitors to NHKR may be produced using methods which are generally known in the art. A particular method involves the use of purified NHKR to produce antibodies or to screen libraries of pharmaceutical agents for those which specifically bind NHKR.

Antibodies which are specific for NHKR may be used directly as an antagonist, or indirectly as a targeting or delivery mechanism for bringing a pharmaceutical agent to cells or tissue which express NHKR. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with NHKR or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to NHKR have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of NHKR amino acids may be fused with those of another protein such as keyhole limpet hemocyanin and antibody produced against the chimeric molecule.

Monoclonal antibodies to NHKR may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce NHKR-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for NHKR may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between NHKR and its specific antibody. A two-site, monoclonal-based immunoassay utilizing monoclonal antibodies reactive to two non-interfering NHKR epitopes is preferred, but a competitive binding assay may also be employed (Maddox, supra).

In another embodiment of the invention, the polynucleotides encoding NHKR, or any fragment thereof, or antisense molecules, may be used for therapeutic purposes. In one aspect, antisense to the polynucleotide encoding NHKR may be used in situations in which it would be desirable to block the transcription of the mRNA. In particular, cells may be transformed with sequences complementary to polynucleotides encoding NHKR. Thus, antisense molecules may be used to modulate NHKR activity, or to achieve regulation of gene function. Such technology is now well known in the art, and sense or antisense oligomers or larger fragments, can be designed from various locations along the coding or control regions of sequences encoding NHKR.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding NHKR. These techniques are described both in Sambrook et al. (supra) and in Ausubel et al. (supra).

Genes encoding NHKR can be turned off by transforming a cell or tissue with expression vectors which express high levels of a polynucleotide or fragment thereof which encodes NHKR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding NHKR, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding NHKR.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding NHKR. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of NHKR, antibodies to NHKR, mimetics, agonists, antagonists, or inhibitors of NHKR. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores.

Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of NHKR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example NHKR or fragments thereof, antibodies of NHKR, agonists, antagonists or inhibitors of NHKR, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind NHKR may be used for the diagnosis of conditions or diseases characterized by expression of NHKR, or in assays to monitor patients being treated with NHKR, agonists, antagonists or inhibitors. The antibodies useful for diagnostic purposes may be prepared in the same manner as those described above for therapeutics. Diagnostic assays for NHKR include methods which utilize the antibody and a label to detect NHKR in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring NHKR are known in the art and provide a basis for diagnosing altered or abnormal levels of NHKR expression. Normal or standard values for NHKR expression are established by combining body fluids or cell extracts taken from normal mammalian subjects, preferably human, with antibody to NHKR under conditions suitable for complex formation The amount of standard complex formation may be quantified by various methods, but preferably by photometric, means. Quantities of NHKR expressed in subject samples, control and disease, from biopsied tissues are compared with the standard values. Deviation between standard and subject values establishes the parameters for diagnosing disease.

In another embodiment of the invention, the polynucleotides encoding NHKR may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of NHKR may be correlated with disease. The diagnostic assay may be used to distinguish between absence, presence, and excess expression of NHKR, and to monitor regulation of NHKR levels during therapeutic intervention.

In one aspect, hybridization with PCR probes which are capable of detecting polynucleotide sequences, including genomic sequences, encoding NHKR or closely related molecules, may be used to identify nucleic acid sequences which encode NHKR. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding NHKR, alleles, or related sequences.

Probes may also be used for the detection of related sequences, and should preferably contain at least 50% of the nucleotides from any of the NHKR encoding sequences. The hybridization probes of the subject invention may be DNA or RNA and derived from the nucleotide sequence of SEQ ID NO:2 or from genomic sequence including promoter, enhancer elements, and introns of the naturally occurring NHKR.

Means for producing specific hybridization probes for DNAs encoding NHKR include the cloning of nucleic acid sequences encoding NHKR or NHKR derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding NHKR may be used for the diagnosis of conditions or diseases which are associated with expression of NHKR. Examples of such conditions or diseases include hypothyroidism, hypercholerolemia, dysmyelination, and antigen processing deficiencies. The polynucleotide sequences encoding NHKR may be used in Southern or northern analysis, dot blot, or other membrane-based technologies; in PCR technologies; or in dip stick, pin, ELISA or chip assays utilizing fluids or tissues from patient biopsies to detect altered NHKR expression. Such qualitative or quantitative methods are well known in the art.

In a particular aspect, the nucleotide sequences encoding NHKR may be useful in assays that detect activation or induction of various cancers, particularly those mentioned above. The nucleotide sequences encoding NHKR may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding NHKR in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of NHKR, a normal or standard profile for expression is established. This may be accomplished by combining body fluids or cell extracts taken from normal subjects, either animal or human, with a sequence, or a fragment thereof, which encodes NHKR, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding NHKR may involve the use of PCR. Such oligomers may be chemically synthesized, generated enzymatically, or produced from a recombinant source. Oligomers will preferably consist of two nucleotide sequences, one with sense orientation (5'->3') and another with antisense (3<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of NHKR include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode NHKR may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981 f). Correlation between the location of the gene encoding NHKR on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, NHKR, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between NHKR and the agent being tested, may be measured.

Another technique for drug screening which may be used provides for high throughput screening of compounds having suitable binding affinity to the protein of interest as described in published PCT application WO84/03564. In this method, as applied to NHKR large numbers of different small test compounds are synthesized on a solid substrate, such as plastic pins or some other surface. The test compounds are reacted with NHKR, or fragments thereof, and washed. Bound NHKR is then detected by methods well known in the art. Purified NHKR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding NHKR specifically compete with a test compound for binding NHKR. In this manner, the antibodies can be used to detect the presence of any peptide which shares one or more antigenic determinants with NHKR.

In additional embodiments, the nucleotide sequences which encode NHKR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I PROSNOT01 cDNA Library Construction

The prostate tissue used for library construction was obtained from a 78 year-old Caucasian male with leukemia (Lot No. 94-039, International Institute for the Advancement of Medicine, Exton Pa.). The tissue was flash frozen, ground in a mortar and pestle, lysed immediately in buffer containing guanidinium isothiocyanate and spun through cesium chloride. The lysate was extracted twice with phenol chloroform at pH 8.0 and centrifuged over a CsCl cushion using an Beckman SW28 rotor in a Beckman L8-70M Ultracentrifuge (Beckman Instruments). The RNA was precipitated using 0.3 M sodium acetate and 2.5 volumes of ethanol, resuspended in water and DNase treated for 15 min at 37° C. The RNA was isolated using the Qiagen Oligotex kit (QIAGEN Inc, Chatsworth Calif.) and used to construct the cDNA library.

First strand cDNA synthesis was accomplished using an oligo d(T) primer/linker which also contained an XhoI restriction site. Second strand synthesis was performed using a combination of DNA polymerase I, *E. coli* ligase and RNase H, followed by the addition of an EcoRI adaptor to the blunt ended cDNA. The EcoRI adapted, double-stranded cDNA was then digested with XhoI restriction enzyme and fractionated on Sephacryl S400 to obtain sequences which exceeded 1000 bp in size. The size selected cDNAs were inserted into the LAMBDAZAP vector system (Stratagene, La Jolla Calif.); and the vector, which contains the pBLUESCRIPT phagemid (Stratagene), was transformed into cells of *E. coli*, strain XL1-BLUEMRF (Stratagene).

The phagemid forms of individual cDNA clones were obtained by the in vivo excision process. Enzymes from both pBluescript and a cotransformed fl helper phage nicked the DNA, initiated new DNA synthesis, and created the smaller, single-stranded circular phagemid DNA molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

II Isolation and Sequencing of cDNA Clones

Plasmid DNA was released from the cells and purified using the Miniprep Kit (Catalogue #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog #22711, LIFE TECHNOLOGIES, Gaithersburg Md.) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS™ DNA Purification System (Catalogue #A7100, Promega, Madison Wis.) or QIAWELL-8 Plasmid, QlAwell PLUS DNA and QIAwell ULTRA DNA Purification Systems (QIAGEN Inc., Chatsworth Calif.).

The cDNAs were sequenced by the method of Sanger F and A R Coulson (1975; J. Mol. Biol. 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as Gen-Bank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding NHKR occurs. Abundance and percent abundance are also reported. Abundance directly reflects the number of times a particular transcript is represented in a cDNA library, and percent abundance is abundance divided by the total number of sequences examined in the cDNA library.

V Extension of NHKR-Encoding Polynucleotides to Full Length or to Recover Regulatory Sequences Full length NHKR-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2xCarb. The following day, several colonies are randomly picked from each plate and cultured in 150 µl of liquid LB/2xCarb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3x) containing 4 units of rTth DNA polymerase, a vector primer, and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of $[\gamma\text{-}^{32}P]$ adenosine triphosphate (Amersham) and T4 polynucleotide kinase (DUPONT NEN, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DUPONT NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1xsaline sodium citrate and 0.5% sodium dodecyl sulfate. After XOMAT AR film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the NHKR-encoding sequence, or any part thereof, is used to inhibit in vivo or in vitro expression of naturally occurring NHKR. Although use of antisense oligonucleotides, comprising about 20 base-pairs, is specifically described, essentially the same procedure is used with larger cDNA fragments. An oligonucleotide based on the coding sequences of NHKR, as shown in FIGS. 1A, 1B and 1C, is used to inhibit expression of naturally occurring NHKR. The complementary oligonucleotide is designed from the most unique 5' sequence as shown in FIGS. 1A, 1B and 1C and used either to inhibit transcription by preventing promoter binding to the upstream nontranslated sequence or translation of an NHKR-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A, 1B and 1C.

VIII Expression of NHKR

Expression of NHKR is accomplished by subcloning the cDNAs into appropriate vectors and transforming the vectors into host cells. In this case, the cloning PSPORT1 vector, previously used for the generation of the cDNA library is used to express NHKR in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of NHKR into the bacterial growth media which can be used directly in the following assay for activity.

IX Demonstration of NHKR Activity

Golgi enriched membranes containing NHKR are prepared from cells or tissues and are used to demonstrate the specific binding of a synthetic peptides containing the KDEL sequence to the NHKR. The tissues or cells are fragmented in a Dounce homogenizer, centrifuged at 1,500×g, and the postnuclear supernate recovered. This supernate is spun at 100,000×g, the crude membrane pellet is retrieved and incubated with 100 mM $Na_2CO_3$ for 10 min. at 4° C. to expose the luminal membrane surface. The binding assay consists of membranes (0.5–1.0 ug of protein), $1×10^5$ cpm of $^{125}I$ labled KDEL-sequence peptide (0.5 ng of peptide), and varying amounts of competitor peptide in a final concentration of 20 mM NaCl, 250 ug $ml^{-1}$ bovine serum albumin, and 50 mM sodium cacodylate, pH 5.0. The assay mixtures are incubated at 4° C. for 20 min. or until equilibrium is reached. Following pelleting in a microfuge at 4° C. for 5 min., the supernates are removed and the membranes are counted in a Gamma Counter. The KDEL peptide sequence consists of YTSEKDEL (corresponding to the 7 carboxy-terminal residues of the mammalian protein BiP), the negative control peptide has the sequence LNYFDDEL. To assay the specificity of the binding, competition binding is performed with a variety of unlabeled peptides (Wilson D. W. (1993) J. Biol. Chem. 268:7465–7468).

X Production of NHKR Specific Antibodies

NHKR that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using finoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring NHKR Using Specific Antibodies

Naturally occurring or recombinant NHKR is substantially purified by immunoaffinity chromatography using antibodies specific for NHKR. An immunoaffinity column is constructed by covalently coupling NHKR antibody to an activated chromatographic resin, such as CnBr-activated Sepharose (Pharmacia & Upjohn). After the coupling, the resin is blocked and washed according to the manufacturer's instructions.

Media containing NHKR is passed over the immunoaffinity column, and the column is washed under conditions that allow the preferential absorbance of NHKR (e.g., high ionic strength buffers in the presence of detergent). The column is eluted under conditions that disrupt antibody/NHKR binding (eg, a buffer of pH 2–3 or a high concentration of a chaotrope, such as urea or thiocyanate ion), and NHKR is collected.

XII Identification of Molecules Which Interact with NHKR

NHKR or biologically active fragments thereof are labeled with $^{125}I$ Bolton-Hunter reagent (Bolton et al. (1973) Biochem. J. 133: 529). Candidate molecules previously arrayed in the wells of a multi-well plate are incubated with the labeled NHKR, washed and any wells with labeled NHKR complex are assayed. Data obtained using different concentrations of NHKR are used to calculate values for the number, affinity, and association of NHKR with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Various modifications of the described modes for carrying out the invention which are obvious to those skilled in molecular biology or related fields are intended to be within the scope of the following claims.

What is claimed is:

1. A substantially purified novel human KDEL receptor (NHKR) comprising the amino acid sequence of SEQ ID NO:1.

2. A composition comprising the human KDEL receptor of claim 1 and a suitable carrier.

3. A method to screen a large number of molecules or compounds for their ability to form complexes with the human KDEL receptor of claim 1, the method comprising:
   (a) combining the human KDEL receptor of claim 1 with the compound or molecule under conditions to allow complex formation; and
   (b) detecting complex formation, wherein the presence of the complex identifies a molecule or compound that specifically binds the human KDEL receptor of claim 1.

4. The method of claim 3, wherein the molecules or compounds are chosen from the group consisting of peptides, agonists, antagonists, inhibitors, antibodies and pharmaceutical agents.

5. A method of using the human KDEL receptor of claim 1 to purify a molecule or compound which specifically binds the human KDEL receptor of claim 1 from a sample, the method comprising:
   (a) combining the human KDEL receptor of claim 1 with a sample under conditions to allow specific binding;
   (b) recovering the the human KDEL receptor of claim 1 bound to the molecule or compound; and
   (c) separating the human KDEL receptor of claim 1 from the molecule or compound, thereby obtaining purified molecule or compound.

* * * * *

UNITED STATES PATENT AND TRADEMARK OFFICE
CERTIFICATE OF CORRECTION

PATENT NO.    : 6,103,874
DATED         : August 15, 2000
INVENTOR(S)   : Olga Bandman, Jennifer L. Hillman, Henry Yue, Karl J. Guegler, Neil C. Corley
                Y. Tom Tang and Purvi Shah It is certified that error appears in the above-identified patent and that said Letters Patent is hereby corrected as shown below:

Drawings,
Please replace Figures 2A and 2B with attached Figures 2A and 2B

Signed and Sealed this

Twenty-sixth Day of November, 2002

*Attest:*

*Attesting Officer*

JAMES E. ROGAN
*Director of the United States Patent and Trademark Office*

FIGURE 2A

```
  1  M N V F R I L G D L I H L L A M I L L L G N I W R S K C C K   NFKR
  1  M N L F R F L G D L S H L L A I L L L K I W K S R S C A       GI 119543
  1  M N I F R L T G D L S H L A A I V I L L L K I W K T R S C A   GI 31218

31  G I S G K S Q I L F A L V F T T R Y L D L F T N F I S I Y N   NFKR
 31  G I S G K S Q V L F A V V F T A R Y L D L F T N Y I S L Y N   GI 119543
 31  G I S G K S Q L L F A L V F T T R Y L D L F T S F I S L Y N   GI 31218

61  T V M K V V F L L C A Y V T V Y M I Y G K F R K T F D S E N   NFKR
 61  T C M K V V Y I A C S F T T V W L I Y S K F K A T Y D G N H   GI 119543
 61  T S M K V I Y L A C S Y A T V V Y L I Y L K F K A T Y D G N H   GI 31218

91  D T F R L E F L L V P V I G L S F L E N Y S F T L L E I L W   NFKR
 91  D T F R V E F L V V P T A I L A F L V N H D F T P L E I L W   GI 119543
 91  D T F R V E F L V V P V G G L S F L V N H D F S P L E I L W   GI 31218

121  T F S I Y L E S V A I L P Q L F M I S K T G E A E T I T T H   NFKR
121  T F S I Y L E S V A I L P Q L F M V S K T G E A E T I T S H   GI 119543
121  T F S I Y L E S V A I L P Q L F M I S K T G E A E T I T T H   GI 31218
```

```
151  Y L X F L G L Y R A L Y L A N W I R R Y Q T E N F Y D Q I A   NHKR
151  Y L F A L G V Y R T L Y L F N W I W R Y H F E G F F D L I A   GI 119543
151  Y L F F L G L Y R A L Y L V N W I W R F Y F E G F F D L I A   GI 31218

181  V V S G V V Q T I F Y C D F F Y L V T K V L K G K K L S L     NHKR
181  I V A G L V Q T L V L Y C D F F Y L H T K V L K G K K L S L   GI 119543
181  V V A G V V Q T I L Y C D F F Y L Y I T K V L K G K K L S L   GI 31218

211  P M P I                                                       NHKR
211  P A                                                           GI 119543
211  P A                                                           GI 31218
```

FIGURE 2B

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 214 amino acids
        (B) TYPE: amino acid
        (C) STRANDEDNESS: single
        (D) TOPOLOGY: linear (vii) IMMEDIATE SOURCE:
        (B) CLONE: Consensus (xi) SEQUENCE DESCRIPTION: SEQ ID NO:1:

Met Asn Val Phe Arg Ile Leu Gly Asp Leu Ile His Leu Leu Ala Met
 1               5                  10                  15

Ile Leu Leu Leu Gly Asn Ile Trp Arg Ser Lys Cys Cys Lys Gly Ile
                20                  25                  30

Ser Gly Lys Ser Gln Ile Leu Phe Ala Leu Val Phe Thr Thr Arg Tyr
            35                  40                  45

Leu Asp Leu Phe Thr Asn Phe Ile Ser Ile Tyr Asn Thr Val Met Lys
    50                  55                  60

Val Val Phe Leu Leu Cys Ala Tyr Val Thr Val Tyr Met Ile Tyr Gly
65                  70                  75                  80

Lys Phe Arg Lys Thr Phe Asp Ser Glu Asn Asp Thr Phe Arg Leu Glu
                85                  90                  95

Phe Leu Leu Val Pro Val Ile Gly Leu Ser Phe Leu Glu Asn Tyr Ser
                100                 105                 110

Phe Thr Leu Leu Glu Ile Leu Trp Thr Phe Ser Ile Tyr Leu Glu Ser
            115                 120                 125

Val Ala Ile Leu Pro Gln Leu Phe Met Ile Ser Lys Thr Gly Glu Ala
            130                 135                 140

Glu Thr Ile Thr Thr His Tyr Leu Xaa Phe Leu Gly Leu Tyr Arg Ala
145                 150                 155                 160

Leu Tyr Leu Ala Asn Trp Ile Arg Arg Tyr Gln Thr Glu Asn Phe Tyr
                165                 170                 175

Asp Gln Ile Ala Val Val Ser Gly Val Val Gln Thr Ile Phe Tyr Cys
            180                 185                 190

Asp Phe Phe Tyr Leu Tyr Val Thr Lys Val Leu Lys Gly Lys Lys Leu
            195                 200                 205

Ser Leu Pro Met Pro Ile
    210

(2) INFORMATION FOR SEQ ID NO:2:

(i) SEQUENCE CHARACTERISTICS:
        (A) LENGTH: 1073 base pairs
        (B) TYPE: nucleic acid
        (C) STRANDEDNESS: single
        (D) TOPOLOGY: linear (vii) IMMEDIATE SOURCE:
        (B) CLONE: Consensus (xi) SEQUENCE DESCRIPTION: SEQ ID NO:2:

TGGCAGCCGC CCTGCCCGCC AGAAAGTTTC CCCCTAAGTT TGCTGGGCGC GGGCGCACGA      60

```
CTGACTGGCT GGACCATGAA CGTGTTCCGA ATCCTCGGCG ACCTGATCCA CCTCCTGGCC      120

ATGATCTTGC TGCTGGGGAA TATCTGGAGG TCCAAGTGCT GCAAGGGCAT CTCTGGGAAA      180

AGCCAGATCC TGTTTGCTCT CGTCTTCACC ACCAGGTACC TGGACCTGTT CACCAACTTC      240

ATCTCCATCT ACAACACAGT AATGAAGGTG GTTTTTCTCC TCTGTGCCTA TGTTACAGTG      300

TACATGATAT ATGGGAAATT CCGTAAAACT TTTGACAGTG AGAATGACAC ATTCCGCCTG      360

GAGTTTCTTC TGGTCCCAGT CATTGGCCTT TCCTTCCTTG AAAACTACAG TTTCACTCTG      420

CTGGAGATCC TCTGGACTTT CTCTATCTAT CTGGAATCAG TGGCTATCCT GCCCCAGCTC      480

TTCATGATCA GCAAGACTGG AGAGGCTGAG ACCATAACTA CTCACTACCT GTNCTTTCTG      540

GGTCTGTACC GGGCACTCTA CCTGGCTAAC TGGATCAGGC GGTACCAGAC TGAGAATTTC      600

TATGACCAAA TTGCAGTCGT GTCTGGAGTA GTACAAACCA TCTTCTACTG TGACTTCTTC      660

TACTTGTATG TGACCAAAGT CCTTAAGGGA AGAAGTTAA GTCTTCCAAT GCCAATCTGA      720

GGACCTTCAG AGACAGTCTA CGCCTTAACA AGCACATGAA GGAAACTNTT TTGAATGTTC      780

TCTTTGGCAA CTTATCCATA ATTTGGGATC AAATGTTAAA ACCAGAAAAG TGTTTAGTGT      840

GGATTTCAGC AAAACCTGAT CATCCCACCC AGAAGACCTT CTCATCAATA GATCGCCCTT      900

AAAGACCCAT TGTAAGGTCA TAAAAAACCT CGGCCAACTG CACAAAGATG GTGCCTCACT      960

GCAACAAGAA ACCTTAAGGT GTCTTACCGA CGNAATAAAA AACATAAATG ATTGTTCTCC     1020

TCTTAGAATG TCCCAACTAA AGACCAGTTA AAATATTAGG GTACGTTCTT GTG           1073

(2) INFORMATION FOR SEQ ID NO:3:

(i) SEQUENCE CHARACTERISTICS:
        (A) LENGTH: 212 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 31218

(xi) SEQUENCE DESCRIPTION: SEQ ID NO:3:

Met Asn Ile Phe Arg Leu Thr Gly Asp Leu Ser His Leu Ala Ala Ile
1               5                   10                  15

Val Ile Leu Leu Leu Lys Ile Trp Lys Thr Arg Ser Cys Ala Gly Ile
            20                  25                  30

Ser Gly Lys Ser Gln Leu Leu Phe Ala Leu Val Phe Thr Thr Arg Tyr
        35                  40                  45

Leu Asp Leu Phe Thr Ser Phe Ile Ser Leu Tyr Asn Thr Ser Met Lys
    50                  55                  60

Val Ile Tyr Leu Ala Cys Ser Tyr Ala Thr Val Tyr Leu Ile Tyr Leu
65                  70                  75                  80

Lys Phe Lys Ala Thr Tyr Asp Gly Asn His Asp Thr Phe Arg Val Glu
                85                  90                  95

Phe Leu Val Val Pro Val Gly Gly Leu Ser Phe Leu Val Asn His Asp
            100                 105                 110

Phe Ser Pro Leu Glu Ile Leu Trp Thr Phe Ser Ile Tyr Leu Glu Ser
        115                 120                 125

Val Ala Ile Leu Pro Gln Leu Phe Met Ile Ser Lys Thr Gly Glu Ala
    130                 135                 140

Glu Thr Ile Thr Thr His Tyr Leu Phe Phe Leu Gly Leu Tyr Arg Ala
145                 150                 155                 160
```

```
Leu Tyr Leu Val Asn Trp Ile Trp Arg Phe Tyr Phe Glu Gly Phe Phe
                165                 170                 175

Asp Leu Ile Ala Val Val Ala Gly Val Val Gln Thr Ile Leu Tyr Cys
            180                 185                 190

Asp Phe Phe Tyr Leu Tyr Ile Thr Lys Val Leu Lys Gly Lys Lys Leu
        195                 200                 205

Ser Leu Pro Ala
    210
```

(2) INFORMATION FOR SEQ ID NO:4:

(i) SEQUENCE CHARACTERISTICS:
        (A) LENGTH: 212 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 119543

(xi) SEQUENCE DESCRIPTION: SEQ ID NO:4:

```
Met Asn Leu Phe Arg Phe Leu Gly Asp Leu Ser His Leu Leu Ala Ile
 1               5                  10                  15

Ile Leu Leu Leu Lys Ile Trp Lys Ser Arg Ser Cys Ala Gly Ile
            20                  25                  30

Ser Gly Lys Ser Gln Val Leu Phe Ala Val Val Phe Thr Ala Arg Tyr
            35                  40                  45

Leu Asp Leu Phe Thr Asn Tyr Ile Ser Leu Tyr Asn Thr Cys Met Lys
 50                  55                  60

Val Val Tyr Ile Ala Cys Ser Phe Thr Thr Val Trp Leu Ile Tyr Ser
 65                  70                  75                  80

Lys Phe Lys Ala Thr Tyr Asp Gly Asn His Asp Thr Phe Arg Val Glu
                85                  90                  95

Phe Leu Val Val Pro Thr Ala Ile Leu Ala Phe Leu Val Asn His Asp
                100                 105                 110

Phe Thr Pro Leu Glu Ile Leu Trp Thr Phe Ser Ile Tyr Leu Glu Ser
        115                 120                 125

Val Ala Ile Leu Pro Gln Leu Phe Met Val Ser Lys Thr Gly Glu Ala
    130                 135                 140

Glu Thr Ile Thr Ser His Tyr Leu Phe Ala Leu Gly Val Tyr Arg Thr
145                 150                 155                 160

Leu Tyr Leu Phe Asn Trp Ile Trp Arg Tyr His Phe Glu Gly Phe Phe
                165                 170                 175

Asp Leu Ile Ala Ile Val Ala Gly Leu Val Gln Thr Val Leu Tyr Cys
            180                 185                 190

Asp Phe Phe Tyr Leu Tyr Ile Thr Lys Val Leu Lys Gly Lys Lys Leu
        195                 200                 205

Ser Leu Pro Ala
    210
```

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:5:

-continued

```
Tyr Thr Ser Glu Lys Asp Glu Leu
1               5

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:6:

Leu Asn Tyr Phe Asp Asp Glu Leu
1               5
```